United States Patent

Yoshikawa

(10) Patent No.: US 7,498,459 B2
(45) Date of Patent: Mar. 3, 2009

(54) METHOD FOR PRODUCING (1-ALKENYL)CYCLOPROPANE COMPOUND

(75) Inventor: Koji Yoshikawa, Toyonaka (JP)

(73) Assignee: Sumitomo Chemical Company, Limited, Tokyo (JP)

(*) Notice: Subject to any disclaimer, the term of this patent is extended or adjusted under 35 U.S.C. 154(b) by 0 days.

(21) Appl. No.: 10/599,072

(22) PCT Filed: Mar. 18, 2005

(86) PCT No.: PCT/JP2005/005614

§ 371 (c)(1),
(2), (4) Date: Sep. 19, 2006

(87) PCT Pub. No.: WO2005/090280

PCT Pub. Date: Sep. 29, 2005

(65) Prior Publication Data

US 2007/0197818 A1   Aug. 23, 2007

(30) Foreign Application Priority Data

Mar. 22, 2004  (JP)  ............... 2004-082145
Mar. 22, 2004  (JP)  ............... 2004-082146

(51) Int. Cl.
*C07C 69/74* (2006.01)
(52) U.S. Cl. .................. 560/124; 562/505; 562/506
(58) Field of Classification Search ............. 562/505, 562/506; 560/124
See application file for complete search history.

(56) References Cited

U.S. PATENT DOCUMENTS

| | | | |
|---|---|---|---|
| 4,048,215 A * | 9/1977 | Krief et al. ................ | 560/124 |
| 4,233,129 A * | 11/1980 | Franck-Neumann et al. ................ | 204/157.87 |
| 4,288,387 A * | 9/1981 | Crosby et al. .............. | 558/366 |
| 4,296,241 A * | 10/1981 | Hoffmann et al. .......... | 560/124 |
| 4,401,673 A | 8/1983 | Martel et al. | |
| 4,537,897 A * | 8/1985 | Tessier et al. ............... | 514/351 |
| 4,565,822 A * | 1/1986 | Tessier et al. ............... | 514/351 |
| 4,709,085 A * | 11/1987 | Nugent et al. ............... | 560/124 |
| 4,879,302 A | 11/1989 | Tessier et al. | |

FOREIGN PATENT DOCUMENTS

| | | |
|---|---|---|
| EP | 1 609 777 A1 | 12/2005 |
| GB | 1285350 | 8/1972 |
| JP | 56-113737 A | 9/1981 |
| JP | 58-164542 A | 9/1983 |
| JP | 63-122661 A | 5/1988 |
| JP | 2004-307480 A | 11/2004 |

OTHER PUBLICATIONS

L. Crombie et al, "Syntheses of [14]C-Labelled (+)-*trans*-Chrysanthemum Mono- and Di- carboxylic Acids, and of Related Compounds", J. Chem. Soc. (C), 1970, pp. 1076-1080.

M. Elliott et al., "The Pyrethrins and Related compounds, Part XVIII.[1] Insecticidal 2,2- Dimethylcyclopropanecarboxylates with New Unsaturated 3-Substituents", J.C.S. Perkin Trans. I, 1974, pp. 2470-2474.

E. Bosone et al., "Synthesis and Insecticidal Activity of 3-(Haloalkyl-1,3-dienyl)-2,2- dimethylcyclopropanecarboxylates", Pestic. Sci., 17, 1986, pp. 621-630.

M. Matsui et al., "Studies on Chrysanthemic Acid. IV. Synthesis of Chrysanthemumdicarboxylic Acid for Chrysanthemic Acid", Proc. Japan Acad., vol. 32, No. 5, 1956, pp. 353-355.

N. Hoffman et al., "Palladium-Catalyzed Decarbonylation of trans-α-Substituted Cinnamaldehydes", J. Org. Chem., vol. 27, Jul. 1962, pp. 2687-2689.

H.E. Eschinazi et al., "Study in the Terpene Series.XXXI.[1] Synthesis of Apopinene by Catalytic Decarbonylation of Myrtenal", J. Org. Chem., vol. 24, Sep. 1959, pp. 1369.

2,2-Di:methyl cyclopropane carboxylic acids prodn.—by de:carbonylating di:methyl formyl:cyclopropane carboxylic acid, used as stabilizers for beta-lactam antibiotics, XP-002468679, Database WPI Week 198345, Sep. 29, 1983, Derwent Publications Ltd., London.

Masanao, et al., Studies on chrysanthemic acid. XV. Selenium dioxide oxidation of tert-butyl (.+-.)-trans-chrysanthemate. The isolation of tert-butyl (.+-.)-trans-2,2-dimethyl-3-(2-formyl-3-hydroxy-1-propenyl) cyclopropanecarboxylate, XP-002468677, Database CA, Chemical Abstracts Service.

Tetsu, et al., Three-bond carbon-13-proton coupling constants for chrysanthemic acid and phenothrin metabolites: detection by two-dimensional long-range 13C-1H J-resolution spectroscopy, Database CA, Chemical Abstracts Service.

* cited by examiner

*Primary Examiner*—Shailendra Kumar
(74) *Attorney, Agent, or Firm*—Sughrue Mion, PLLC

(57) ABSTRACT

A method for producing a (1-alkenyl)cyclopropane compound represented by the formula (2):

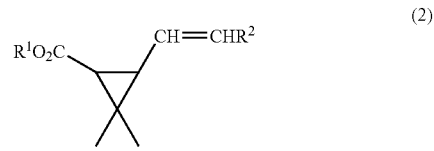

(2)

wherein $R^1$ and $R^2$ are the same or different, and independently represent a hydrogen atom, an optionally substituted alkyl group, an optionally substituted alkenyl group, an optionally substituted alkynyl group, an optionally substituted aryl group or an optionally substituted aralkyl group, which comprises bringing a (2-formyl-1-alkenyl)cyclopropane compound represented by the formula (1):

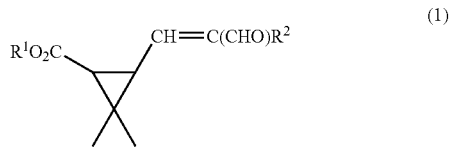

(1)

wherein $R^1$ and $R^2$ are the same as defined above, into contact with a palladium catalyst.

3 Claims, No Drawings

METHOD FOR PRODUCING (1-ALKENYL)CYCLOPROPANE COMPOUND

TECHNICAL FIELD

The present invention relates to a method for producing a (1-alkenyl)cyclopropane compound which is an important compound as a synthetic intermediate of pyrethroid type household agents for epidemic prevention and insecticides, and a method for producing the synthetic intermediate thereof.

BACKGROUND ART

A (1-alkenyl)cyclopropane compound such as 2,2-dimethyl-3-(1-propenyl)cyclopropanecarboxylic acid ester is an important compound, for example, as a synthetic intermediate of pyrethroid type household agents for epidemic prevention and insecticides. As a method for producing it, for example, a method which comprises subjecting Wittig reaction to a formylcyclopropane compound such as 2,2-dimethyl-3-formylcyclopropanecarboxylic acid ester has been known (e.g. Non-patent document 1). However, it has some problems which are use of excess amount of expensive Wittig agent and environmental burden caused by phosphorous waste and the method was not unsatisfactory as an industrial method.

Non-patent document 1: J. Chem. Soc. (C), 1076 (1970)

DISCLOSURE OF THE INVENTION

According to the present invention, a (1-alkenyl)cyclopropane compound which is an important compound as a synthetic intermediate of pyrethroid type household agents for epidemic prevention and insecticides can be industrially advantageously produced.

That is, the present invention relates to a method for producing a (1-alkenyl)cyclopropane compound represented by the formula (2):

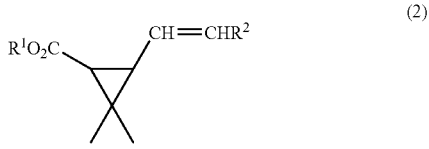

(2)

wherein $R^1$ and $R^2$ are the same or different, and independently represent a hydrogen atom, an optionally substituted alkyl group, an optionally substituted alkenyl group, an optionally substituted alkynyl group, an optionally substituted aryl group or an optionally substituted aralkyl group, which comprises bringing a (2-formyl-1-alkenyl)cyclopropane compound represented by the formula (1):

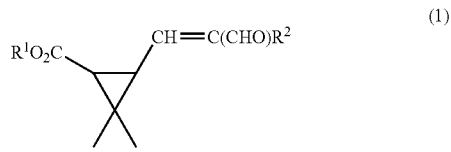

(1)

wherein $R^1$ and $R^2$ are the same as defined above, into contact with a palladium catalyst, and a novel method for producing the above-mentioned formula (1).

BEST MODE FOR CARRYING OUT THE PRESENT INVENTION

First, a (2-formyl-1-alkenyl)cyclopropane compound (hereinafter, simply referred to as the (2-formyl-1-alkenyl) cyclopropane compound (1)) will be illustrated.

Among the optionally substituted alkyl group represented by $R^1$ in the formula of the (2-formyl-1-alkenyl)cyclopropane compound (1), examples of the unsubstituted alkyl group include a straight chain, branched chain or cyclic alkyl group having 1 to 10 carbon atoms such as a methyl, ethyl, n-propyl, isopropyl, n-butyl, isobutyl, sec-butyl, tert-butyl, n-pentyl, cyclopentyl, n-hexyl, cyclohexyl and menthyl group. These alkyl groups may be substituted with a substituent or substituents such as a halogen atom such as a fluorine atom; an alkoxy group such as a methoxy, ethoxy, n-propoxy, isopropoxy, n-butoxy, isobutoxy and tert-butoxy group; an aryloxy group such as a phenoxy group; and an aralkyloxy group such as a benzyloxy group. Examples of the alkyl group substituted with the substituent or substituents include a 2-fluoroethyl, pentafluoroethyl, 2-methoxyethyl, 2-ethoxyethyl, 2-phenoxyethyl and 2-benzyloxyethyl group.

Among the optionally substituted alkenyl group represented by $R^1$, examples of the unsubstituted alkenyl group include a straight chain, branched chain or cyclic alkenyl group having 2 to 10 carbon atoms such as a 2-propenyl, 2-butenyl, 3-butenyl, 2-methyl-2-propenyl and 2-cyclohexenyl group. These alkenyl groups may be substituted with a substituent or substituents such as a halogen atom such as a fluorine atom; an alkoxy group such as a methoxy, ethoxy, n-propoxy, isopropoxy, n-butoxy, isobutoxy and tert-butoxy group; an aryloxy group such as a phenoxy group; an aralkyloxy group such as a benzyloxy group; and an optionally substituted aryl group such as a phenyl, naphthyl, 4-fluorophenyl, 2-methylphenyl, 4-methoxyphenyl and 4-phenoxyphenyl group. Examples of the alkenyl group substituted with the substituent or substituents include a 3-fluoro-2-propenyl, 3,3-difluoro-2-propenyl, 4-methoxy-2-butenyl, 4-phenoxy-2-butenyl, 4-benzyloxy-2-butenyl and 3-phenyl-2-propenyl group.

Among the optionally substituted alkynyl group represented by $R^1$, examples of the unsubstituted alkynyl group include a straight chain or branched chain alkynyl group having 2 to 10 carbon atoms such as a 2-propynyl, 2-butynyl, 2-pentynyl and 4-methyl-2-pentynyl group. These alkynyl groups may be substituted with a substituent or substituents such as a halogen atom such as a fluorine atom; an alkoxy group such as a methoxy, ethoxy, n-propoxy, isopropoxy, n-butoxy, isobutoxy and tert-butoxy group; an aryloxy group such as a phenoxy group; an aralkyloxy group such as a benzyloxy group; and an optionally substituted aryl group such as a phenyl, naphthyl, 4-fluorophenyl, 2-methylphenyl, 4-methoxyphenyl and 4-phenoxyphenyl group. Examples of the alkynyl group substituted with the substituent or substituents include a 4-fluoro-2-butynyl, 4-methoxy-2-butynyl, 4-phenoxy-2-butynyl and 4-benzyloxy-2-butynyl group.

Among the optionally substituted aryl group represented by $R^1$, examples of the unsubstituted aryl group include an aryl group having 6 to 10 carbon atoms such as a phenyl and naphthyl group. These aryl groups may be substituted with a substituent or substituents such as a halogen atom such as a fluorine atom; an alkoxy group such as a methoxy, ethoxy, n-propoxy, isopropoxy, n-butoxy, isobutoxy and tert-butoxy group; an aryloxy group such as a phenoxy group; an aralkyloxy group such as a benzyloxy group; and the above-mentioned optionally substituted alkyl group. Examples of the aryl group substituted with the substituent or substituents include a 4-fluorophenyl, 2-methylphenyl, 4-methoxyphenyl and 4-phenoxyphenyl group.

The optionally substituted aralkyl group represented by $R^1$ represents a group which is composed of the above-mentioned optionally substituted alkyl group and the above-mentioned optionally substituted aryl group. Preferable examples thereof include an unsubstituted aralkyl group having 7 to 8 carbon atoms (for example, a benzyl and phenethyl group) or an aralkyl group having 7 to 8 carbon atoms substituted with at least one group selected from a fluorine atom, an alkyl group having 1 to 3 carbon atom (for example, a methyl, ethyl and propyl group), an alkoxy group having 1 to 3 carbon atoms (for example, a methoxy, ethoxy and propoxy group) and an alkoxyalkyl group having 2 to 3 carbon atoms (for example, a methoxymethyl, ethoxymethyl and methoxyethyl group). More detail, examples thereof include a benzyl, phenethyl, methylbenzyl, methoxybenzyl, phenoxybenzyl, 2,3,5,6-tetrafluorobenzyl, 2,3,5,6-tetrafluoro-4-methylbenzyl, 2,3,5,6-tetrafluoro-4-methoxybenzyl and 2,3,5,6-tetrafluoro-4-methoxymethylbenzyl group.

As $R^1$, preferred are the straight chain, branched chain or cyclic alkyl group having 1 to 10 carbon atoms, the unsubstituted aralkyl group having 7 to 8 carbon atoms, and the aralkyl group having 7 to 8 carbon atoms substituted with at least one group selected from a fluorine atom, an alkyl group having 1 to 3 carbon atoms, an alkoxy group having 1 to 3 carbon atoms and an alkoxyalkyl group having 2 to 3 carbon atoms. Among the above-mentioned straight chain, branched chain or cyclic alkyl group having 1 to 10 carbon atoms, the straight chain alkyl group having 1 to 4 carbon atoms is more preferable.

Among the optionally substituted alkyl group represented by $R^2$, examples of the unsubstituted alkyl group include a straight chain, branched chain or cyclic alkyl group having 1 to 10 carbon atoms such as a methyl, ethyl, n-propyl, isopropyl, n-butyl, isobutyl, sec-butyl, tert-butyl, n-pentyl, cyclopentyl, n-hexyl, cyclohexyl and menthyl group. These alkyl groups may be substituted with a substituent or substituents such as a halogen atom such as a fluorine atom; an alkoxy group such as a methoxy, ethoxy, n-propoxy, isopropoxy, n-butoxy, isobutoxy and tert-butoxy group (preferably an alkoxy group having 1 to 4 carbon atoms); an alkoxycarbonyl group such as a methoxycarbonyl, ethoxycarbonyl, n-propoxycarbonyl, isopropoxycarbonyl, n-butoxycarbonyl, isobutoxycarbonyl and tert-butoxycarbonyl group; an aryloxy group such as a phenoxy group; an aryloxycarbonyl group such as a phenoxycarbonyl group; an aralkyloxy group such as a benzyloxy group; and an aralkyloxycarbonyl group such as a benzyloxycarbonyl group. Examples of the alkyl group substituted with the substituent or substituents include a 2-fluoroethyl, pentafluoroethyl, 2-methoxyethyl, 2-ethoxyethyl, 2-phenoxyethyl, 2-benzyloxyethyl and 2-methoxycarbonylethyl group.

Among the optionally substituted alkenyl group represented by $R^2$, examples of the unsubstituted alkenyl group include a straight chain, branched chain or cyclic alkenyl group having 2 to 10 carbon atoms such as a vinyl, 1-propenyl, 1-butenyl, 2-propenyl, 2-butenyl, 3-butenyl, 2-methyl-2-propenyl and 2-cyclohexenyl group. These alkenyl groups may be substituted with a substituent or substituents such as a halogen atom such as a fluorine atom; an alkoxy group such as a methoxy, ethoxy, n-propoxy, isopropoxy, n-butoxy, isobutoxy and tert-butoxy group; an alkoxycarbonyl group such as a methoxycarbonyl, ethoxycarbonyl, n-propoxycarbonyl, isopropoxycarbonyl, n-butoxycarbonyl, isobutoxycarbonyl and tert-butoxycarbonyl group; an aryloxy group such as a phenoxy group; an aryloxycarbonyl group such as a phenoxycarbonyl group; an aralkyloxy group such as a benzyloxy group; an aralkyloxycarbonyl group such as a benzyloxycarbonyl group; and an optionally substituted aryl group such as a phenyl, naphthyl, 4-fluorophenyl, 2-methylphenyl, 4-methoxyphenyl, 4-phenoxyphenyl and 4-methoxycarbonylphenyl group. Examples of the alkenyl group substituted with the substituent or substituents include a 3,3,3-trifluoro-1-propenyl, 3,3-difluoro-2-propenyl, 4-methoxy-2-butenyl, 4-phenoxy-2-butenyl, 4-benzyloxy-2-butenyl, 2-phenylvinyl, 3-phenyl-2-propenyl and 3-methoxycarbonyl-2-propenyl group.

Among the optionally substituted alkynyl group represented by $R^2$, examples of the unsubstituted alkynyl group include a straight chain or branched chain alkynyl group having 2 to 10 carbon atoms such as an ethynyl, 1-propynyl, 2-propynyl, 2-butynyl, 2-pentynyl and 4-methyl-2-pentynyl group. These alkynyl groups may be substituted with a substituent or substituents such as a halogen atom such as a fluorine atom; an alkoxy group such as a methoxy, ethoxy, n-propoxy, isopropoxy, n-butoxy, isobutoxy and tert-butoxy group; an alkoxycarbonyl group such as a methoxycarbonyl, ethoxycarbonyl, n-propoxycarbonyl, isopropoxycarbonyl, n-butoxycarbonyl, isobutoxycarbonyl and tert-butoxycarbonyl group; an aryloxy group such as a phenoxy group; an aryloxycarbonyl group such as a phenoxycarbonyl group; an aralkyloxy group such as a benzyloxy group; an aralkyloxycarbonyl group such as a benzyloxycarbonyl group; and an optionally substituted aryl group such as a phenyl, naphthyl, 4-fluorophenyl, 2-methylphenyl, 4-methoxyphenyl, 4-phenoxyphenyl and 4-methoxycarbonylphenyl group. Examples of the alkynyl group substituted with the substituent or substituents include a 3-fluoro-1-propynyl, 2-phenylethynyl, 4-methoxy-2-butynyl, 4-phenoxy-2-butynyl, 4-benzyloxy-2-butynyl and 4-methoxycarbonyl-2-butynyl group.

Among the optionally substituted aryl group represented by $R^2$, examples of the unsubstituted aryl group include an aryl group having 6 to 10 carbon atoms such as a phenyl and naphthyl group. These aryl groups may be substituted with a substituent or substituents such as a halogen atom such as a fluorine atom; an optionally substituted alkyl group such as a methyl, ethyl, n-propyl, isopropyl, n-butyl, isobutyl, sec-butyl, tert-butyl, n-pentyl, cyclopentyl, n-hexyl, cyclohexyl, menthyl, 2-fluoroethyl, pentafluoroethyl, 2-methoxyethyl, 2-ethoxyethyl, 2-phenoxyethyl, 2-benzyloxyethyl and 2-methoxycarbonylethyl group; an alkoxy group such as a methoxy, ethoxy, n-propoxy, isopropoxy, n-butoxy, isobutoxy and tert-butoxy group; an alkoxycarbonyl group such as a methoxycarbonyl, ethoxycarbonyl, n-propoxycarbonyl, isopropoxycarbonyl, n-butoxycarbonyl, isobutoxycarbonyl and tert-butoxycarbonyl group; an aryloxy group such as a phenoxy group; an aryloxycarbonyl group such as a phenoxycarbonyl group; an aralkyloxy group such as a benzyloxy group; and an aralkyloxycarbonyl group such as a benzyloxycarbonyl group. Examples of the aryl group substituted with the substituent or substituents include a 4-fluorophenyl, 2-methylphenyl, 4-methoxyphenyl, 4-phenoxyphenyl and 4-methoxycarbonylphenyl group.

Examples of the optionally substituted aralkyl group represented by $R^2$ include groups which are composed of optionally substituted alkyl groups such as a methyl, ethyl, n-propyl, isopropyl, n-butyl, isobutyl, sec-butyl, tert-butyl, n-pentyl, cyclopentyl, n-hexyl, cyclohexyl, menthyl, 2-fluoroethyl, pentafluoroethyl, 2-methoxyethyl, 2-ethoxyethyl, 2-phenoxyethyl, 2-benzyloxyethyl and 2-methoxycarbonylethyl group and optionally substituted aryl groups such as a phenyl, naphthyl, 4-fluorophenyl, 2-methylphenyl, 4-methoxyphenyl, 4-phenoxyphenyl and 4-methoxycarbonylphenyl group. More detail, unsaturated aralkyl groups having 7 to 8 carbon atoms (for example, a benzyl and phenethyl group) and aralkyl groups having 7 to 8 carbon atoms substituted with at least one group selected from a fluorine atom, an alkyl group having 1 to 3 carbon atoms (for example, a methyl, ethyl and propyl group), an alkoxy group having 1 to 3 carbon atoms (for example, a methoxy, ethoxy and propoxy group) and an alkoxyalkyl group having 2 to 3 carbon atoms (for example, a methoxymethyl, ethoxymethyl and methoxyethyl group) are exemplified. Specifically, a benzyl, phenethyl, methylbenzyl, methoxybenzyl, phenoxybenzyl, 2,3,5,6-tetrafluorobenzyl, 2,3,5,6-tetrafluoro-4-methylbenzyl, 2,3,5,6-tetrafluoro-4-methoxybenzyl and 2,3,5,6-tetrafluoro-4-methoxymethylbenzyl groups are exemplified.

As the preferable $R^2$, a straight chain, branched chain or cyclic alkyl group having 1 to 7 carbon atoms, an alkenyl group having 3 to 5 carbon atoms or an alkynyl group having 3 to 5 carbon atoms, a straight chain, branched chain or cyclic alkyl group having 1 to 7 carbon atoms substituted with a fluorine atom or atoms, a phenyl group or groups or an alkoxy group or groups having 1 to 3 carbon atoms, an alkenyl having 3 to 5 carbon atoms substituted with a fluorine atom or atoms, a phenyl group or groups or an alkoxy group or groups having 1 to 3 carbon atoms, and an alkynyl group having 3 to 5 carbon atoms substituted with a fluorine atom or atoms, a phenyl group or groups or an alkoxy group or groups having 1 to 3 carbon atoms are exemplified.

In the above-mentioned (2-formyl-1-alkenyl)cyclopropane compound (1), the compound wherein $R^2$ is a hydrogen atom or a methyl group is disclosed in Journal of the Chemical Society, Perkin Transactions 1, (1974), (21), 2470-4, Pesticide Science (1986), 17(6), 621-30, CAS No. 100520-73-8, EP33259, Pesticide Science (1986), 17(6), 621-30, Proc. Japan Acad. (1956), 32 353-5 and CAS No. 93807-76-2.

When $R^2$ represents that other than a hydrogen atom or a methyl group in the (2-formyl-1-alkenyl)cyclopropane compound (1), the (2-formyl-1-alkenyl)cyclopropane compound (1) is a novel compound.

Specific examples of the (2-formyl-1-alkenyl)cyclopropane compound (1) include 2,2-dimethyl-3-(2-formyl-1-propenyl)cyclopropanecarboxylic acid, methyl 2,2-dimethyl-3-(2-formyl-1-propenyl)cyclopropanecarboxylate, ethyl 2,2-dimethyl-3-(2-formyl-1-propenyl)cyclopropanecarboxylate, n-propyl 2,2-dimethyl-3-(2-formyl-1-propenyl)cyclopropanecarboxylate, isopropyl 2,2-dimethyl-3-(2-formyl-1-propenyl)cyclopropanecarboxylate, n-butyl 2,2-dimethyl-3-(2-formyl-1-propenyl)cyclopropanecarboxylate, isobutyl 2,2-dimethyl-3-(2-formyl-1-propenyl)cyclopropanecarboxylate, tert-butyl 2,2-dimethyl-3-(2-formyl-1-propenyl)cyclopropanecarboxylate, 2-propenyl 2,2-dimethyl-3-(2-formyl-1-propenyl)cyclopropanecarboxylate, 2-propynyl 2,2-dimethyl-3-(2-formyl-1-propenyl)cyclopropanecarboxylate, phenyl 2,2-dimethyl-3-(2-formyl-1-propenyl)cyclopropanecarboxylate, 1-naphthyl 2,2-dimethyl-3-(2-formyl-1-propenyl)cyclopropanecarboxylate, benzyl 2,2-dimethyl-3-(2-formyl-1-propenyl)cyclopropanecarboxylate, 3-phenoxybenzyl 2,2-dimethyl-3-(2-formyl-1-propenyl)cyclopropanecarboxylate, 2,3,5,6-tetrafluorobenzyl 2,2-dimethyl-3-(2-formyl-1-propenyl)cyclopropanecarboxylate, 2,3,5,6-tetrafluoro-4-methylbenzyl 2,2-dimethyl-3-(2-formyl-1-propenyl)cyclopropanecarboxylate, 2,3,5,6-tetrafluoro-4-methoxybenzyl 2,2-dimethyl-3-(2-formyl-1-propenyl)cyclopropanecarboxylate, 2,3,5,6-tetrafluoro-4-methoxymethylbenzyl 2,2-dimethyl-3-(2-formyl-1-propenyl)cyclopropanecarboxylate, 2,2-dimethyl-3-(2-formyl-1-hexenyl)cyclopropanecarboxylic acid, methyl 2,2-dimethyl-3-(2-formyl-1-hexenyl)cyclopropanecarboxylate, ethyl 2,2-dimethyl-3-(2-formyl-1-hexenyl)cyclopropanecarboxylate, 2,2-dimethyl-3-(2-formyl-3,3,3-trifluoro-1-propenyl)cyclopropanecarboxylic acid, methyl 2,2-dimethyl-3-(2-formyl-3,3,3-trifluoro-1-propenyl)cyclopropanecarboxylate, ethyl 2,2-dimethyl-3-(2-formyl-3,3,3-trifluoro-1-propenyl)cyclopropanecarboxylate, 2,2-dimethyl-3-(2-formyl-1,3-hexadienyl)cyclopropanecarboxylic acid, methyl 2,2-dimethyl-3-(2-formyl-1,3-hexadienyl)cyclopropanecarboxylate, ethyl 2,2-dimethyl-3-(2-formyl-1,3-hexadienyl)cyclopropanecarboxylate, 2,2-dimethyl-3-(2-formyl-1-buten-3-ynyl)cyclopropanecarboxylic acid, methyl 2,2-dimethyl-3-(2-formyl-1-buten-3-ynyl)cyclopropanecarboxylate, ethyl 2,2-dimethyl-3-(2-formyl-1-buten-3-ynyl)cyclopropanecarboxylate, 2,2-dimethyl-3-(2-formyl-2-phenylethenyl)cyclopropanecarboxylic acid, methyl 2,2-dimethyl-3-(2-formyl-2-phenylethenyl)cyclopropanecarboxylate, ethyl 2,2-dimethyl-3-(2-formyl-2-phenylethenyl)cyclopropanecarboxylate, 2,2-dimethyl-3-(2-formyl-3-phenyl-1-propenyl)cyclopropanecarboxylic acid, methyl 2,2-dimethyl-3-(2-formyl-3-phenyl-1-propenyl)cyclopropanecarboxylate and ethyl 2,2-dimethyl-3-(2-formyl-3-phenyl-1-propenyl)cyclopropanecarboxylate.

The (2-formyl-1-alkenyl)cyclopropane compound (1) has two asymmetric carbon atoms on a cyclopropane ring and a double bond and has eight kinds of stereoisomers. Any one of the isomers or a mixture wherein they are mixed in any ratio can be used in the method of the present invention.

A method for producing the (2-formyl-1-alkenyl)cyclopropane compound (1) is not particularly limited and for example, a known method such as a method which comprises oxidizing a chrysanthemic acid ester using selenium dioxide (e.g. J. Chem. Soc. (C), 1076(1970)) may be used and in the point of avoiding use of highly toxic selenium dioxide, a method which comprises reacting a formylcyclopropane compound represented by the formula (3):

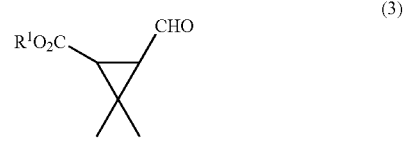

(3)

wherein $R^1$ is the same as defined above (hereinafter, simply referred to as the formylcyclopropane compound (3)), with an aldehyde compound represented by the formula (4):

(4)

wherein $R^2$ is the same as defined above (hereinafter, simply referred to as the aldehyde compound (4) is preferable particularly as a industrial method.

The reaction of the formylcyclopropane compound (3) and the aldehyde compound (4) is usually conducted by reacting both in the presence of a base.

Examples of the formylcyclopropane compound (3) include 2,2-dimethyl-3-formylcyclopropanecarboxylic acid, methyl 2,2-dimethyl-3-formylcyclopropanecarboxylate, ethyl 2,2-dimethyl-3-formylcyclopropanecarboxylate,
n-propyl 2,2-dimethyl-3-formylcyclopropanecarboxylate,
isopropyl 2,2-dimethyl-3-formylcyclopropanecarboxylate,
n-butyl 2,2-dimethyl-3-formylcyclopropanecarboxylate,
isobutyl 2,2-dimethyl-3-formylcyclopropanecarboxylate,
tert-butyl 2,2-dimethyl-3-formylcyclopropanecarboxylate,
2-propenyl 2,2-dimethyl-3-formylcyclopropanecarboxylate,
2-propynyl 2,2-dimethyl-3-formylcyclopropanecarboxylate,
phenyl 2,2-dimethyl-3-formylcyclopropanecarboxylate,
1-naphthyl 2,2-dimethyl-3-formylcyclopropanecarboxylate,
2-naphthyl 2,2-dimethyl-3-formylcyclopropanecarboxylate,
benzyl 2,2-dimethyl-3-formylcyclopropanecarboxylate,
3-phenoxybenzyl 2,2-dimethyl-3-formylcyclopropanecarboxylate, 2,3,5,6-tetrafluorobenzyl 2,2-dimethyl-3-formylcyclopropanecarboxylate, 2,3,5,6-tetrafluoro-4-methylbenzyl 2,2-dimethyl-3-formylcyclopropanecarboxylate, 2,3,5,6-tetrafluoro-4-methoxybenzyl 2,2-dimethyl-3-formylcyclopropanecarboxylate and 2,3,5,6-tetrafluoro-4-methoxymethylbenzyl 2,2-dimethyl-3-formylcyclopropanecarboxylate.

The formylcyclopropane compound (3) has two asymmetric carbon atoms on a cyclopropane ring and has four kinds of isomers. Any one of the isomers or a mixture wherein they are mixed in any ratio can be used in the method of the present invention.

Examples of the aldehyde compound (4) include acetaldehyde, propanal, butanal, hexanal, cyclohexylacetaldehyde, 3-methylbutanal, 3,3-dimethylbutanal, 3,3,3-trifluoropropanal, 3-methoxypropanal, phenylacetaldehyde, 3-phenylpropanal, trans-3-hexenal, trans-4-phenyl-3-butenal, 3-butynal, 3-pentynal, 4-pentynal and 4-phenyl-3-butynal.

The amount of the aldehyde compound (4) to be used is usually in the range of 0.7 to 5 moles relative to 1 mole of the formylcyclopropane compound (3) and the purpose is accomplished. It is preferably in the range of about 1 to 2 moles.

Examples of the base used in the present reaction include an alkali metal alkoxide such as sodium methoxide and potassium tert-butoxide; an alkali metal hydroxide such as sodium hydroxide and potassium hydroxide; a secondary amine such as pyrrolidine, piperidine, morpholine, dimethylamine and diethylamine; and a primary amine such as n-butylamine, n-hexylamine and aniline. Among them, the primary or secondary amine compound is preferable and pyrolidine or piperidine is more preferably used. When the primary or secondary amine compound is used, it may be formed a salt with an acid described below in the reaction system. The amount of the base to be used is usually in the range of 0.05 to 1 mole relative to 1 mole of the formylcyclopropane compound (3) and the purpose is accomplished. It is preferably in the range of about 0.1 to 0.5 mole.

When the primary or secondary amine compound is used as the base in the present reaction, the reaction can be also carried out in the coexistence of an acid to improve the reactivity. The acid coexisted in this case is usually a Bronsted acid. Examples thereof include an inorganic acid such as phosphoric acid and carbonic acid; a saturated aliphatic carboxylic acid such as acetic acid, propionic acid and hexanoic acid; an aromatic carboxylic acid such as benzoic acid and salicylic acid; an unsaturated aliphatic carboxylic acid such as maleic acid and fumaric acid; a hydroxycarboxylic acid such as mandelic acid, tartaric acid and malic acid; and a cyclopropanecarboxylic acid having the structure of which the formylcyclopropane compound (3) is oxidized such as 3,3-dimethylcyclopropane-1,2-dicarboxylic acid and 3-(methoxycarbonyl)-2,2-dimethylcyclopropanecarboxylic acid. Preferred is a carboxylic acid such as the saturated aliphatic carboxylic acid, the aromatic carboxylic acid, the unsaturated aliphatic carboxylic acid, the hydroxycarboxylic acid and the cyclopropanecarboxylic acid. The amount of the acid to be used is usually 0.01 to 2 moles, preferably about 0.05 to 1 mole relative to 1 mole of the primary or secondary amine compound.

The reaction of the formylcyclopropane compound (3) and the aldehyde compound (4) can be carried out without using an inert solvent and it is usually carried out in the presence of the inert solvent. Examples of the solvent include water; an aromatic hydrocarbon solvent such as toluene, xylene, mesitylene and chlorobenzene; an aliphatic hydrocarbon solvent such as pentane, hexane, heptane, octane and cyclohexane; an ester solvent such as ethyl acetate and dimethyl carbonate; a halogenated aliphatic hydrocarbon solvent such as dichloromethane, dichloroethane and carbon tetrachloride; a nitrile solvent such as acetonitrile and benzonitrile; an ether solvent such as diethyl ether and tetrahydrofuran; and an alcohol solvent such as methanol, ethanol and isopropyl alcohol. These solvents may be used alone or by mixing two or more thereof. The amount of the solvent to be used is not particularly limited and it is usually about 0.5 to 10 parts by weight, preferably about 1 to 5 parts by weight relative to 1 part by weight of the formylcyclopropane compound (3).

The reaction temperature is usually in the range of −20 to 120° C., preferably in the range of about 0 to 70° C.

The mixing order in the present invention is not particularly limited and the aldehyde compound (4) is preferably added into the mixed liquid obtained by dissolving the formylcyclopropane compound (3) and the base, if necessary in the solvent. In that case, the aldehyde compound (4) may be used as it is and by diluting in the above-mentioned reaction solvent. The aldehyde compound (4) is usually added over 1 hour or more, preferably 3 hours or more. The upper limit is not particularly limited and it is accordingly selected in consideration of the productivity. When the primary or secondary amine compound is used as the base and the reaction is carried out in the presence of the acid, they are preferably previously mixed with the mixed liquid before adding the aldehyde compound (4).

After completion of the reaction, an organic layer containing the desired (2-formyl-1-alkenyl)cyclopropane compound (1) can be respectively obtained by removing water produced in the reaction by separation in the case of using a water-immiscible solvent such as toluene, cyclohexane and monochlorobenzene as the reaction solvent; by removing a water-miscible solvent by concentration, followed by carrying the extract operation using a water-immiscible solvent such as toluene and xylene in the case of using the water-miscible solvent such as acetonitrile and methanol; and by carrying extract operation using a water-immiscible solvent such as toluene and xylene in the case of conducting the reaction without using the inert solvent. The organic layer containing the (2-formyl-1-alkenyl)cyclopropane compound (1) obtained may be used as the solution to the decarbonylation reaction described below, if necessary after washing with water, an aqueous sodium carbonate or the like, and may be concentrated to obtain the (2-formyl-1-alkenyl)cyclopropane compound (1), and it may be used to the decarbonylation reaction. The (2-formyl-1-alkenyl)cyclopropane compound (1) obtained is further purified by a conventional purification means such as distillation and column chromatography and then it can be used to the decarbonylation reaction.

In the production of the (2-formyl-1-alkenyl)cyclopropane compound (1), an optically active (2-formyl-1-alkenyl)cyclopropane compound (1) is usually obtained as the product by using an optically active formylcyclopropane compound (3) as the raw material.

Next, the decarbonylation reaction which comprises bringing the (2-formyl-1-alkenyl)cyclopropane compound (1) into contact with a palladium catalyst to obtain a (1-alkenyl)cyclopropane compound represented by the formula (2) (hereinafter, simply referred to as the (1-alkenyl)cyclopropane compound (2)) will be illustrated.

Examples of the palladium catalyst include metal palladium; a zerovalent palladium complex such as tetrakis(triphenylphosphine)palladium(0), tris(tricyclohexylphosphine)palladium(0) and bis(dibenzylideneacetone)palladium(0); a divalent palladium complex such as bis(triphenylphosphine)palladium(II) dichloride, bis(tricyclohexylphosphine)palladium(II) dichloride, bis(benzonitrile)palladium(II) dichloride, bis(acetonitrile)palladium(II) dichloride, dichloro(1,5-cyclooctadiene)palladium(II), [1,1'-bis(diphenylphosphino)ferrocene]palladium(II) dichloride and palladium(II) acetylacetonate; a divalent palladium salt such as palladium(II) acetate, palladium(II) trifluoroacetate, palladium(II) chloride, palladium(II) nitrate and palladium(II) iodide; and a palladium supported on a solid such as palladium/carbon, palladium/silica-alumina, palladium/silica, palladium/alumina and palladium(II) acetate/silica.

The amount of the palladium catalyst (as a palladium atom for the palladium supported on the solid) to be used is usually in the range of 0.01 to 10 mole % relative to 1 mole of the (2-formyl-1-alkenyl)cyclopropane compound (1) and the object is accomplished. Preferred is in the range of about 0.2 to 5 mole %.

The decarbonylation reaction of the (2-formyl-1-alkenyl)cyclopropane compound (1) can be conducted without using an inert solvent and it is usually conducted in the presence of the inert solvent. Examples of the solvent include an aromatic hydrocarbon solvent such as benzene, toluene, xylene, mesitylene, cymene and chlorobenzene; an aliphatic hydrocarbon solvent such as hexane, cyclohexane, heptane, octane, decane and hexadecane; an unsaturated aliphatic hydrocarbon solvent such as hexene, heptene, octene, decene, hexadecene, cyclohexene and cyclododecene; an ester solvent such as ethyl acetate and ethyl octanoate; a halogenated aliphatic hydrocarbon solvent such as dichloroethane, carbon tetrachloride and octyl chloride; a nitrile solvent such as acetonitrile and benzonitrile; an ether solvent such as tert-butyl methyl ether, tetrahydrofuran and dihexyl ether; and a ketone solvent such as methyl isobutyl ketone and 5-nonanone. They may be used alone or in the form of a mixed solvent. The amount thereof to be used is not particularly limited and usually about 0.5 to 100 parts by weight, preferably about 1 to 10 parts by weight relative to 1 part by weight of the (2-formyl-1-alkenyl)cyclopropane compound (1).

When a palladium catalyst containing moisture is used, the catalyst may be mixed with the above-mentioned reaction solvent and moisture may be previously removed by using a means such as an azeotropic dehydration.

The reaction temperature is usually 70 to 250° C., preferably about 100 to 180° C. The reaction time varies depending on the reaction temperature and it is usually about 3 to 30 hours.

The present reaction is usually conducted under atmospheric pressure condition. In the case of conducting at a reaction temperature of the boiling point of the solvent used and above, it may be conducted under pressurized condition.

After the decarbonylation reaction, the (1-alkenyl)cyclopropane compound (2) or a solution thereof can be obtained by distilling the product or conducting filtration operation to remove the palladium catalyst in the case of the catalyst supported on a solid. The (1-alkenyl)cyclopropane compound (2) or the solution thereof may be further purified by a conventional purification means such as concentration, distillation and column chromatography.

Examples of the (1-alkenyl)cyclopropane compound (2) thus obtained include 2,2-dimethyl-3-(1-propenyl)cyclopropanecarboxylic acid, methyl 2,2-dimethyl-3-(1-propenyl)cyclopropanecarboxylate, ethyl 2,2-dimethyl-3-(1-propenyl)cyclopropanecarboxylate, n-propyl 2,2-dimethyl-3-(1-propenyl)cyclopropanecarboxylate, isopropyl 2,2-dimethyl-3-(1-propenyl)cyclopropanecarboxylate, n-butyl 2,2-dimethyl-3-(1-propenyl)cyclopropanecarboxylate, isobutyl 2,2-dimethyl-3-(1-propenyl)cyclopropanecarboxylate, tert-butyl 2,2-dimethyl-3-(1-propenyl)cyclopropanecarboxylate, 2-propenyl 2,2-dimethyl-3-(1-propenyl)cyclopropanecarboxylate, 2-propynyl 2,2-dimethyl-3-(1-propenyl)cyclopropanecarboxylate, phenyl 2,2-dimethyl-3-(1-propenyl)cyclopropanecarboxylate, 1-naphthyl 2,2-dimethyl-3-(1-propenyl)cyclopropanecarboxylate, 2-naphthyl 2,2-dimethyl-3-(1-propenyl)cyclopropanecarboxylate, benzyl 2,2-dimethyl-3-(1-propenyl)cyclopropanecarboxylate, 3-phenoxybenzyl 2,2-dimethyl-3-(1-propenyl)cyclopropanecarboxylate, 2,3,5,6-tetrafluorobenzyl 2,2-dimethyl-3-(1-propenyl)cyclopropanecarboxylate, 2,3,5,6-tetrafluoro-4-methylbenzyl 2,2-dimethyl-3-(1-propenyl)cyclopropanecarboxylate, 2,3,6-tetrafluoro-4-methoxybenzyl 2,2-dimethyl-3-(1-propenyl)cyclopropanecarboxylate, 2,3,5,6-tetrafluoro-4-methoxymethylbenzyl 2,2-dimethyl-3-(1-propenyl)cyclopropanecarboxylate, 2,2-dimethyl-3-(1-hexenyl)cyclopropanecarboxylic acid, methyl 2,2-dimethyl-3-(1-hexenyl)cyclopropanecarboxylate, ethyl 2,2-dimethyl-3-(1-hexenyl)cyclopropanecarboxylate, 2,2-dimethyl-3-(3,3,3-trifluoro-1-propenyl)cyclopropanecarboxylic acid, methyl 2,2-dimethyl-3-(3,3,3-trifluoro-1-propenyl)cyclopropanecarboxylate, ethyl 2,2-dimethyl-3-(3,3,3-trifluoro-1-propenyl)cyclopropanecarboxylate, 2,2-dimethyl-3-(1,3-hexadienyl)cyclopropanecarboxylic acid, methyl 2,2-dimethyl-3-(1,3-hexadienyl)cyclopropanecarboxylate, ethyl 2,2-dimethyl-3-(1,3-hexadienyl)cyclopropanecarboxylate, 2,2-dimethyl-3-(1-buten-3-ynyl)cyclopropanecarboxylic acid, methyl 2,2-dimethyl-3-(1-buten-3-ynyl)cyclopropanecarboxylate, ethyl 2,2-dimethyl-3-(1-buten-3-ynyl)cyclopropanecarboxylate, 2,2-dimethyl-3-(2-phenylethenyl)cyclopropanecarboxylic acid, methyl 2,2-dimethyl-3-(2-phenylethenyl)cyclopropanecarboxylate, ethyl 2,2-dimethyl-3-(2-phenylethenyl)cyclopropanecarboxylate, 2,2-dimethyl-3-(3-phenyl-1-propenyl)cyclopropanecarboxylic acid, methyl 2,2-dimethyl-3-(3-phenyl-1-propenyl)cyclopropanecarboxylate and ethyl 2,2-dimethyl-3-(3-phenyl-1-propenyl)cyclopropanecarboxylate.

In the present decarbonylation reaction, an optically active (1-alkenyl)cyclopropane compound (2) is usually obtained as the product by using the (2-formyl-1-alkenyl)cyclopropane compound (1) as the raw material.

EXAMPLES

The present invention will be further illustrated in detail by Examples. The present invention is not limited to these Examples. The analysis was carried out by gas chromatography and each purity, each content and the Z/E ratio were respectively calculated by area percentage (%), internal standard method (% by weight) and area percentage.

Example 1

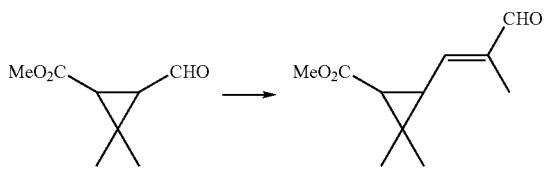

9.6 g of pyrrolidine and 10.8 g of 80% acetic acid were added to 441.9 g of a toluene solution of methyl 2,2-dimethyl-3-formyl-cyclopropanecarboxylate (content: 30.5% by weight) and then 67.4 g of propanal was added dropwise thereto at an inner temperature of 55° C. over 10 hours. After keeping at the same temperature for 1 hour, water produced was removed by separation. The organic layer was washed three times with 42 g of water and separated. Next, after washing once with 14 g of 10% by weight aqueous sodium carbonate and separating, the organic layer obtained was concentrated under reduced pressure. Further, after adding 100 g of water thereto and concentrating under reduced pressure to remove the by-product 2-methyl-2-pentenal, 183.2 g of a xylene solution containing methyl 2,2-dimethyl-3-[(1E)-2-formyl-1-propenyl]cyclopropanecarboxylate was obtained by adding 100 g of xylene thereto and concentrating under reduced pressure. The content was 85.7% by weight and the yield was 93%.

Example 2

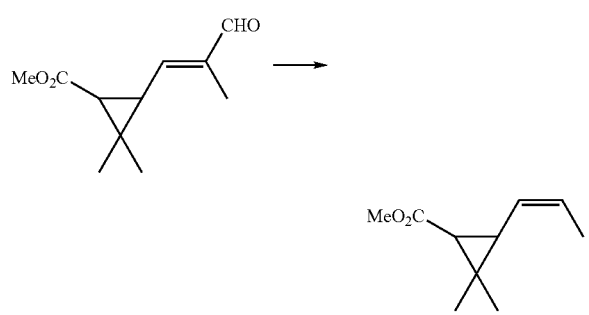

2.40 g of 5% by weight palladium/carbon (50% by weight wet product) and 36 g of xylene were mixed and the mixture was heated to 140° C. to remove moisture by azeotropic dehydration. 26.8 g of the xylene solution of methyl 2,2-dimethyl-3-[(1E)-2-formyl-1-propenyl]cyclopropanecarboxylate (content: 85.7% by weight) obtained in Example 1 and 6 g of xylene were added thereto and the mixture was heated to 150° C. and heated under reflux at the same temperature for 14 hours. After cooling, palladium/carbon was removed by filtration and the filtration residue was washed with xylene to obtain 88.5 g of a xylene solution containing methyl 2,2-dimethyl-3-(1-propenyl)cyclopropanecarboxy-late. The content was 21.5% by weight. The yield was 96%. The conversion was 98%. The Z/E of the double bond was 97/3.

Example 3

0.50 g of methyl 2,2-dimethyl-3-[(1E)-2-formyl-1-propenyl]cyclopropanecarboxylate was dissolved in 2.4 g of p-cymene and 0.033 g of tetrakistriphenylphosphine palladium(0) was added thereto. The mixture was heated to 180° C. and stirred at the same temperature for 9.5 hours to obtain a solution containing 0.24 g of methyl 2,2-dimethyl-3-(1-propenyl)cyclopropanecarboxylate. The yield was 56%. The conversion was 73%. The Z/E of the double bond was 96/4.

Example 4

0.20 g of methyl 2,2-dimethyl-3-[(1E)-2-formyl-1-propenyl]cyclopropanecarboxylate was dissolved in 2.0 g of hexadecane and 0.007 g of tristricyclohexylphosphine palladium(0) was added thereto. The mixture was heated to 180° C. and stirred at the same temperature for 11 hours to obtain a solution containing 0.10 g of methyl 2,2-dimethyl-3-(1-propenyl)cyclopropanecarboxylate. The yield was 58%. The conversion was 83%. The Z/E of the double bond was 94/6.

Example 5

0.20 g of methyl 2,2-dimethyl-3-[(1E)-2-formyl-1-propenyl]cyclopropanecarboxylate was dissolved in 2.0 g of hexadecene and 0.021 g of palladium(II) acetate was added thereto. The mixture was heated to 180° C. and stirred at the same temperature for 11 hours to obtain a solution containing 0.14 g of methyl 2,2-dimethyl-3-(1-propenyl)cyclopropanecarboxylate. The yield was 82%. The conversion was 91%. The Z/E of the double bond was 94/6.

Example 6

0.21 g of methyl 2,2-dimethyl-3-[(1E)-2-formyl-1-propenyl]cyclopropanecarboxylate was dissolved in 2.0 g of hexadecene and 0.066 g of 16.6% by weight palladium(II) acetate/silica was added thereto. The mixture was heated to 180° C. and stirred at the same temperature for 1.5 hours to obtain a solution containing 0.16 g of methyl 2,2-dimethyl-3-(1-propenyl)cyclopropanecarboxylate. The yield was 89%. The conversion was 99%. The Z/E of the double bond was 92/8.

Example 7

0.21 g of methyl 2,2-dimethyl-3-[(1E)-2-formyl-1-propenyl]cyclopropanecarboxylate was dissolved in 2.0 g of hexadecene and 0.10 g of 5% by weight palladium/alumina was added thereto. The mixture was heated to 160° C. and stirred at the same temperature for 6.5 hours to obtain a solution containing 0.16 g of methyl 2,2-dimethyl-3-(1-propenyl)cyclopropanecarboxylate. The yield was 89%. The conversion was 99%. The Z/E of the double bond was 95/5.

Example 8

0.21 g of methyl 2,2-dimethyl-3-[(1E)-2-formyl-1-propenyl]cyclopropanecarboxylate was dissolved in 2.0 g of hexadecene and 0.057 g of 5% by weight palladium/alumina was added thereto. The mixture was heated to 160° C. and stirred at the same temperature for 11 hours to obtain a solution containing 0.15 g of methyl 2,2-dimethyl-3-(1-propenyl)cyclopropanecarboxylate. The yield was 83%. The conversion was 91%. The Z/E of the double bond was 99/1.

Example 9

0.21 g of methyl 2,2-dimethyl-3-[(1E)-2-formyl-1-propenyl]cyclopropanecarboxylate was dissolved in 2.0 g of hexadecane and 0.11 g of 5% by weight palladium/carbon (50% by weight wet product) was added thereto. The mixture was heated to 180° C. and stirred at the same temperature for 7.5 hours to obtain a solution containing 0.14 g of methyl 2,2-dimethyl-3-(1-propenyl)cyclopropanecarboxylate. The yield was 78%. The conversion was 94%. The Z/E of the double bond was 99/1.

Example 10

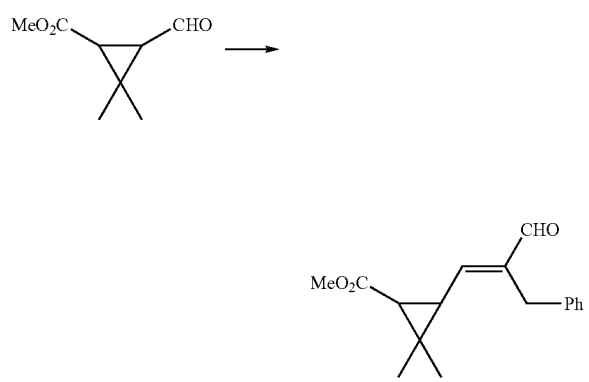

11 g of toluene, 0.71 g of pyrrolidine and 0.62 g of acetic acid were added to 10.4 g of methyl 2,2-dimethyl-3-formylcyclopropanecarboxylate (content: 98.7% by weight) and then a mixed solution of 11.2 g of 3-phenylpropanal and 21 g of toluene was added dropwise thereto at an inner temperature of 55° C. over 6 hours. After keeping at the same temperature for 1 hour, water produced was removed by separation. The organic layer was washed twice with 10 g of water and separated. Next, after washing once with 10 g of 10% by weight aqueous sodium carbonate and separating, the organic layer obtained was concentrated under reduced pressure to obtain 21.4 g of an oily matter. It was purified by silica gel column (hexane:ether=10:2) and the concentration treatment was conducted to obtain 11.2 g of an oily matter containing methyl 2,2-dimethyl-3-[(1E)-3-phenyl-2-formyl-1-propenyl]cyclopropanecarboxylate. Any concentration treatments were conducted with the addition of about 5 mg of 2,6-di-tert-butyl-p-cresol as a stabilizer.

The purity of methyl 2,2-dimethyl-3-[(1E)-3-phenyl-2-formyl-1-propenyl]cyclopropanecarboxylate: 97.3%

Yield: 61%

$^1$H-NMR (300 MHz, CDCl$_3$) δ 1.23 (s, 3H), 1.24 (s, 3H), 1.86 (d, J=5.2 Hz, 1H), 2.48 (dd, J=5.2, 10.2 Hz, 1H), 3.66 (d, J=14.5 Hz, 1H), 3.69 (s, 3H), 3.78 (d, J=14.5 Hz, 1H), 6.23 (d, J=10.2 Hz, 1H), 7.13-7.27 (m, 5H), 9.41 (s, 1H)

$^{13}$C-NMR (75.4 MHz, CDCl$_3$) δ 20.3, 22.3, 29.8, 31.2, 33.3, 37.1, 51.9, 126.1, 128.4, 128.5, 139.2, 144.1, 152.9, 171.0, 193.4

Example 11

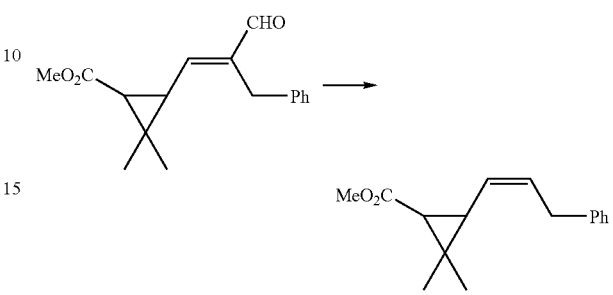

0.82 g of 5% by weight palladium/carbon (50% by weight wet product) and 11 g of xylene were mixed and the mixture was heated to 140° C. to remove moisture by azeotropic dehydration. 5.01 g of methyl 2,2-dimethyl-3-[(1E)-3-phenyl-2-formyl-1-propenyl]cyclopropanecarboxylate (purity: 97.3%) obtained in Example 10 was added thereto and the mixture was heated to 150° C. and heated under reflux at the same temperature for 7 hours. After removing palladium/carbon by filtration, the filtrate was concentrated under reduced pressure to obtain 4.69 g of an oily matter. It was purified by silica gel column (hexane:ethyl acetate=100:3) to obtain 3.63 g of an oily matter containing methyl 2,2-dimethyl-3-(3-phenyl-1-propenyl)cyclopropanecarboxylate.

The purity of methyl 2,2-dimethyl-3-(3-phenyl-1-propenyl)cyclopropanecarboxylate: 78.2%.

Yield: 65%.

$^1$H-NMR (300 MHz, CDCl$_3$) δ 1.16 (s, 3H), 1.28 (s, 3H), 1.53 (d, J=5.4 Hz, 1H), 2.24-2.29 (m, 1H), 3.49 (d, J=7.4 Hz, 2H), 3.68 (s, 3H), 5.20-5.27 (m, 1H), 5.67-5.76 (m, 1H), 7.16-7.33 (m, 5H)

$^{13}$C-NMR (75.5 MHz, CDCl$_3$) δ 20.4, 22.2, 28.8, 31.7, 34.1, 35.0, 51.6, 126.0, 127.3, 128.4, 128.5, 131.3, 140.7, 172.6

Example 12

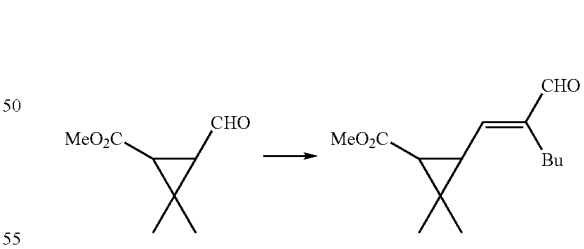

12 g of toluene, 0.72 g of pyrrolidine and 0.62 g of acetic acid were added to 10.8 g of methyl 2,2-dimethyl-3-formylcyclopropanecarboxylate (content: 96.9% by weight) and then a mixed solution of 8.69 g of hexanal and 17 g of toluene was added dropwise thereto at an inner temperature of 55° C. over 6 hours. After keeping at the same temperature for 1 hour, water produced was removed by separation. The organic layer was washed twice with 10 g of water and separated. Next, after washing once with 10 g of 10% by weight aqueous sodium carbonate and separating, the organic layer obtained was concentrated under reduced pressure to obtain 20.1 g of an oily matter. It was purified by silica gel column (hexane:ether=10:1) and the concentration treatment was conducted to obtain 14.1 g of an oily matter containing methyl 2,2-dimethyl-3-[(1E)-2-formyl-1-hexenyl]cyclopropanecarboxylate. Any concentration treatments were conducted with the addition of about 5 mg of 2,6-di-tert-butyl-p-cresol as a stabilizer thereto.

The purity of methyl 2,2-dimethyl-3-[(1E)-2-formyl-1-hexenyl]cyclopropanecarboxylate: 98.1%

Yield: 87%

$^1$H-NMR (300 MHz, CDCl$_3$) δ 0.88-0.93 (m, 3H), 1.24-1.43 (m, 4H), 1.28 (s, 3H), 1.35(s, 3H), 1.86 (d, J=5.2 Hz, 1H), 2.30-2.42 (m, 3H), 3.72 (s, 3H), 6.11 (d, J=10.1 Hz, 1H), 9.33 (s, 1H)

$^{13}$C-NMR (75.4 MHz, CDCl$_3$) δ 13.9, 20.4, 22.4, 23.8, 30.9, 31.0, 33.0, 36.9, 51.9, 145.5, 151.7, 171.3, 193.9

Example 13

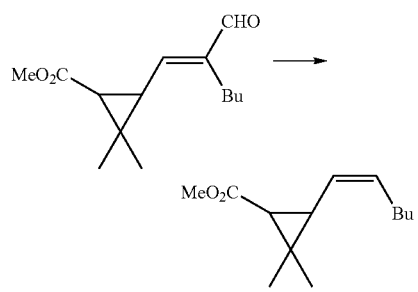

0.92 g of 5% by weight palladium/carbon (50% by weight wet product) and 11 g of xylene were mixed and the mixture was heated to 140° C. to remove moisture by azeotropic dehydration. 5.04 g of methyl 2,2-dimethyl-3-[(1E)-2-formyl-1-hexenyl]cyclopropanecarboxylate (purity: 98.1%) obtained in Example 12 was added thereto and the mixture was heated to 150° C. and heated under reflux at the same temperature for 30 hours. After removing palladium/carbon by filtration, the filtrate was concentrated under reduced pressure to obtain 4.32 g of an oily matter. It was purified by silica gel column (hexane:ether=100:1) to obtain 3.68 g of an oily matter containing methyl 2,2-dimethyl-3-(1-hexenyl)cyclopropanecarboxylate.

The purity of methyl 2,2-dimethyl-3-(1-hexenyl)cyclopropanecarboxylate: 90.8%.

Yield: 77%.

$^1$H-NMR (270 MHz, CDCl$_3$) δ 0.86-0.93 (m, 3H), 1.14 (s, 3H), 1.24-1.39 (m, 4H), 1.45 (d, J=5.3 Hz, 1H), 2.09-2.17 (m, 3H), 3.68 (s, 3H), 5.05-5.13 (m, 1H), 5.46-5.56 (m, 1H)

$^{13}$C-NMR (67.8 MHz, CDCl$_3$) δ 13.9, 20.3, 22.1, 22.2, 27.4, 28.6, 31.7, 31.9, 34.9, 51.4, 126.1, 133.1, 172.7

Example 14

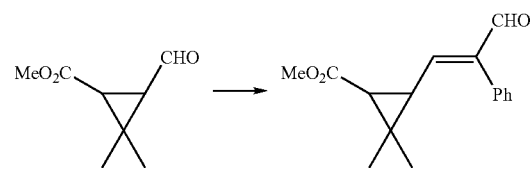

11 g of toluene, 0.76 g of pyrrolidine and 0.69 g of acetic acid were added to 10.3 g of methyl 2,2-dimethyl-3-formylcyclopropanecarboxylate (content: 98.7% by weight) and then a mixed solution of 19.9 g of 50% by weight diethyl phthalate solution of phenylacetaldehyde and 20 g of toluene was added dropwise thereto at an inner temperature of 55° C. over 6 hours. After keeping at the same temperature for 1 hour, water produced was removed by separation. The organic layer was washed twice with 10 g of water and separated. Next, after washing once with 10 g of 10% by weight aqueous sodium carbonate and separating, the organic layer obtained was concentrated under reduced pressure to obtain 29.2 g of an oily matter. It was purified by silica gel column (hexane:ether=10:1) and the concentration treatment was conducted to obtain 17.6 g of an oily matter containing methyl 2,2-dimethyl-3-[(1E)-2-formyl-2-phenylethenyl]cyclopropanecarboxylate. Any concentration treatments were conducted with the addition of about 5 mg of 2,6-di-tert-butyl-p-cresol as a stabilizer thereto.

The purity of methyl 2,2-dimethyl-3-[(1E)-2-formyl-2-phenylethenyl]cyclopropanecarboxylate: 94.8%

Yield: 99%

$^1$H-NMR (270 MHz, CDCl$_3$) δ 1.27 (s, 3H), 1.35 (s, 3H), 1.94 (d, J=5.3 Hz, 1H), 2.35 (dd, J=5.3, 10.2 Hz, 1H), 3.67 (s, 3H), 6.36 (d, J=10.2 Hz, 1H), 7.20-7.45 (m, 5H), 9.57 (s, 1H)

$^{13}$C-NMR (67.8 MHz, CDCl$_3$) δ 20.1, 22.4, 31.5, 33.8, 37.3, 51.8, 128.1, 128.2, 129.6, 132.0, 144.7, 152.8, 170.8, 192.4

Example 15

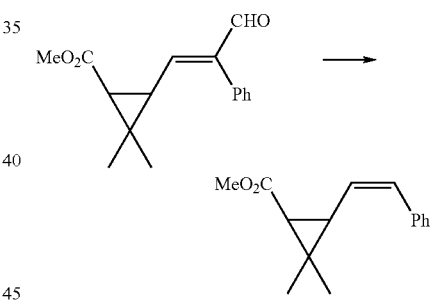

0.91 g of 5% by weight palladium/carbon (50% by weight wet product) and 11 g of xylene were mixed and the mixture was heated to 140° C. to remove moisture by azeotropic dehydration. 4.93 g of methyl 2,2-dimethyl-3-[(1E)-2-formyl-2-phenylethenyl]cyclopropanecarboxylate (purity: 94.8%) obtained in Example 14 was added thereto and the mixture was heated to 150° C. and heated under reflux at the same temperature for 3.5 hours. After removing palladium/carbon by filtration, the filtrate was concentrated under reduced pressure to obtain 4.43 g of an oily matter. It was purified by a silica gel column (hexane:ether/40:1) to obtain 3.57 g of an oily matter containing methyl 2,2-dimethyl-3-(2-phenylethenyl)cyclopropanecarboxylate.

The purity of methyl 2,2-dimethyl-3-(2-phenylethenyl)cyclopropanecarboxylate: 98.4%

Yield: 84%, Z/E ratio of the double bond: 81/19

$^1$H-NMR (270 MHz, CDCl$_3$) δ 1.21 (s, 3H), 1.32 (s, 3H), 1.56 (d, J=5.3 Hz, 1H), 2.39-2.44 (m, 1H), 3.67 (s, 3H), 5.41 (dd, J=8.6, 11.6 Hz, 1H), 6.53 (dd, J=1.3, 11.6 Hz, 1H), 7.19-7.37 (m, 5H)

$^{13}$C-NMR (67.8 MHz, CDCl$_3$) δ 20.1, 22.1, 29.5, 33.0, 35.6, 51.5, 126.9, 128.2, 128.5, 128.7, 131.6, 137.0, 172.2

Example 16

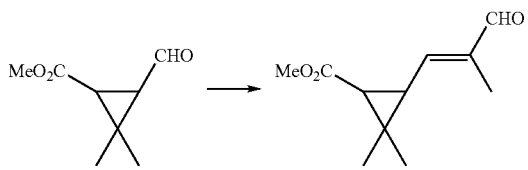

20 g of toluene and 0.89 g of pyrrolidine were added to 20.0 g of methyl 2,2-dimethyl-3-formyl-cyclopropanecarboxylate (content: 98.0% by weight) and then a mixed solution of 8.0 g of propanal and 24 g of toluene was added dropwise thereto at an inner temperature of 60° C. over 6 hours. After keeping at the same temperature for 1 hour, water produced was removed. The organic layer was washed twice with 20 g of water and separated. Next, after washing once with 20 g of 20% by weight aqueous sodium carbonate and separating, the organic layer obtained was concentrated under reduced pressure to obtain 25.1 g of an oily matter containing methyl 2,2-dimethyl-3-[(1E)-2-formyl-1-propenyl]cyclopropanecarboxylate.

The content of methyl 2,2-dimethyl-3-[(1E)-2-formyl-1-propenyl]cyclopropanecarboxylate: 91.5% by weight
Yield: 93%

Example 17

7 g of toluene, 0.78 g of piperidine and 0.51 g of acetic acid were added to 7.0 g of a toluene solution of methyl 2,2-dimethyl-3-formyl-cyclopropanecarboxylate (content: 65.7% by weight) and then a mixed solution of 5.5 g of propanal and 31 g of toluene was added dropwise thereto at an inner temperature of 40° C. for 5 hours. After keeping at the same temperature for 1 hour, water produced was removed by separation. The organic layer was washed twice with 10 g of water and separated. Next, the organic layer obtained was concentrated under reduced pressure to obtain 9.2 g of an oily matter containing methyl 2,2-dimethyl-3-[(1E)-2-formyl-1-propenyl]cyclopropanecarboxylate.

The content of methyl 2,2-dimethyl-3-[(1E)-2-formyl-1-propenyl]cyclopropanecarboxylate: 57.9% by weight
Yield: 92%

Example 18

4 g of toluene, 0.32 g of n-butylamine and 0.27 g of acetic acid were added to 5.4 g of a toluene solution of methyl 2,2-dimethyl-3-formyl-cyclopropanecarboxylate (content: 65.7% by weight) and then a mixed solution of 3.9 g of propanal and 39 g of toluene was added dropwise thereto at an inner temperature of 40° C. over 8 hours. After keeping at the same temperature for 1 hour, water produced was removed by separation. The organic layer was washed twice with 10 g of water and separated. Next, the organic layer obtained was concentrated under reduced pressure to obtain 6.1 g of an oily matter containing methyl 2,2-dimethyl-3-[(1E)-2-formyl-1-propenyl]cyclopropanecarboxylate.

The content of methyl 2,2-dimethyl-3-[(1E)-2-formyl-1-propenyl]cyclopropanecarboxylate: 57.8% by weight
Yield: 79%

Example 19

1.6 g of pyrrolidine and 1.2 g of acetic acid were added to 51.0 g of a cyclohexane solution of methyl 2,2-dimethyl-3-formyl-cyclopropanecarboxylate (content: 34.1% by weight) and then a mixed solution of 9.7 g of propanal and 17 g of cyclohexane was added dropwise thereto at an inner temperature of 40° C. over 4 hours. After keeping at the same temperature for 1 hour, water produced was removed by separation. The organic layer was washed three times with 9 g of water and separated. Next, the organic layer was washed once with 9 g of 20% by weight aqueous sodium carbonate and separated. The organic layer obtained was concentrated under reduced pressure to obtain 23.5 g of an oily matter containing methyl 2,2-dimethyl-3-[(1E)-2-formyl-1-propenyl]cyclopropanecarboxylate.

The content of methyl 2,2-dimethyl-3-[(1E)-2-formyl-1-propenyl]cyclopropanecarboxylate: 84.5% by weight
Yield: 91%

Example 20

1.9 g of pyrrolidine and 1.4 g of acetic acid were added to 80.0 g of a monochlorobenzene solution of methyl 2,2-dimethyl-3-formyl-cyclopropanecarboxylate (content: 25.9% by weight) and then a mixed solution of 11.5 g of propanal and 21 g of monochlorobenzene was added dropwise thereto at an inner temperature of 40° C. over 4 hours. After keeping at the same temperature for 1 hour, water produced was removed by separation. The organic layer was washed three times with 10 g of water and separated. Next, the organic layer was washed once with 10 g of 20% by weight aqueous sodium carbonate and separated. The organic layer obtained was concentrated under reduced pressure to obtain 28.3 g of an oily matter containing methyl 2,2-dimethyl-3-[(1E)-2-formyl-1-propenyl]cyclopropanecarboxylate.

The content of methyl 2,2-dimethyl-3-[(1E)-2-formyl-1-propenyl]cyclopropanecarboxylate: 88.0% by weight
Yield: 96%

Example 21

42 g of acetonitrile, 1.9 g of pyrrolidine and 1.4 g of acetic acid were added to 21.0 g of methyl 2,2-dimethyl-3-formyl-cyclopropanecarboxylate (content: 98.0% by weight) and then a mixed solution of 11.5 g of propanal and 21 g of acetonitrile was added dropwise thereto at an inner temperature of 40° C. over 4 hours. After keeping at the same temperature for 1 hour, acetonitrile was concentrated under reduced pressure. 210 g of toluene was added thereto and washed three times with 10 g of water and separated. Next, the organic layer was washed once with 10 g of 20% by weight aqueous sodium carbonate and separated. The organic layer obtained was concentrated again under reduced pressure to obtain 27.1 g of an oily matter containing methyl 2,2-dimethyl-3-[(1E)-2-formyl-1-propenyl]cyclopropanecarboxylate.

The content of methyl 2,2-dimethyl-3-[(1E)-2-formyl-1-propenyl]cyclopropanecarboxylate: 76.7% by weight
Yield: 80%

Example 22

42 g of methanol, 1.9 g of pyrrolidine and 1.4 g of acetic acid were added to 21.0 g of methyl 2,2-dimethyl-3-formylcyclopropanecarboxylate (content: 98.0% by weight) and then a mixed solution of 11.5 g of propanal and 21 g of methanol was added dropwise thereto at an inner temperature of 40° C. over 4 hours. After keeping at the same temperature for 1 hour, methanol was concentrated under reduced pressure. 210 g of toluene was added thereto and washed three times with 10 g of water and separated. Next, the organic layer was washed once with 10 g of 20% by weight aqueous sodium carbonate and separated. The organic layer obtained was concentrated again under reduced pressure to obtain 24.7 g of an oily matter containing methyl 2,2-dimethyl-3-[(1E)-2-formyl-1-propenyl]cyclopropanecarboxylate.

The content of methyl 2,2-dimethyl-3-[(1E)-2-formyl-1-propenyl]cyclopropanecarboxylate: 74.6% by weight
Yield: 71%

Example 23

4 g of toluene, 0.36 g of pyrrolidine and 0.63 g of benzoic acid were added to 6.5 g of a toluene solution of methyl 2,2-dimethyl-3-formyl-cyclopropanecarboxylate (content: 65.7% by weight) and then a mixed solution of 2.6 g of propanal and 20 g of toluene was added dropwise thereto at an inner temperature of 40° C. over 6 hours. After keeping at the same temperature for 1 hour, water produced was removed. The organic layer was washed twice with 20 g of water and separated. Next, the organic layer was washed once with 20 g of 20% by weight aqueous sodium carbonate and separated. The organic layer obtained was concentrated under reduced pressure to obtain 6.2 g of an oily matter containing methyl 2,2-dimethyl-3-[(1E)-2-formyl-1-propenyl]cyclopropanecarboxylate.

The content of methyl 2,2-dimethyl-3-[(1E)-2-formyl-1-propenyl]cyclopropanecarboxylate: 82.0% by weight
Yield: 94

Example 24

26 g of methanol and 6.4 g of a 28% by weight methanol solution of sodium methylate were added to 21.1 g of a toluene solution of methyl 2,2-dimethyl-3-formyl-cyclopropanecarboxylate (content: 40.5% by weight) at 0° C. and then a mixed solution of 6.4 g of propanal and 6 g of methanol was added dropwise thereto at an inner temperature of 5° C. over 6.5 hours. After keeping at the same temperature for 1 hour, 6.6 g of 10% by weight hydrochloric acid and 89 g of water were added thereto. The extraction treatment was conducted three times with 20 g of toluene. The organic layer obtained was concentrated under reduced pressure to obtain 12.4 g of an oily matter containing methyl 2,2-dimethyl-3-[(1E)-2-formyl-1-propenyl]cyclopropanecarboxylate.

The content of methyl 2,2-dimethyl-3-[(1E)-2-formyl-1-propenyl]cyclopropanecarboxylate: 55.9% by weight
Yield: 65%

INDUSTRIAL APPLICABILITY

According to the present invention, a (1-alkenyl)cyclopropane compound which is an important compound as a synthetic intermediate of pyrethroid type household agents for epidemic prevention and insecticides can be industrially advantageously produced.

The invention claimed is:
1. A method for producing a (1-alkenyl)cyclopropane compound represented by the formula (2):

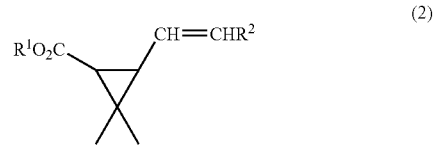

wherein $R^1$ and $R^2$ are the same or different, and independently represent a hydrogen atom, an optionally substituted alkyl group, an optionally substituted alkenyl group, an optionally substituted alkynyl group, an optionally substituted aryl group or an optionally substituted aralkyl group,
which comprises bringing a (2-formyl-1-alkenyl)cyclopropane compound represented by the formula (1):

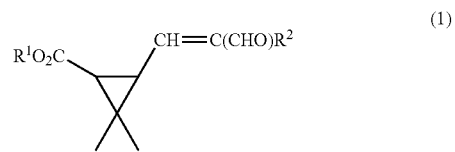

wherein $R^1$ and $R^2$ are the same as defined above, into contact with a palladium catalyst
wherein the (2-formyl-1-alkenyl)cyclopropane compound is obtained by reacting a formylcyclopropane compound represented by the formula (3):

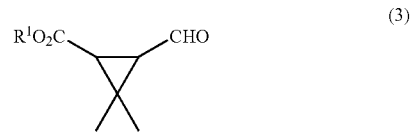

wherein $R^1$ is the same as defined above, with an aldehyde compound represented by the formula (4):

wherein $R^2$ is the same as defined above.

2. The method according to claim 1, wherein $R^1$ represents a straight chain, branched chain or cyclic alkyl group having 1 to 10 carbon atoms, an unsubstituted aralkyl group having 7 to 8 carbon atoms, or an aralkyl group having 7 to 8 carbon atoms substituted with at least one group selected from a fluorine atom, an alkyl group having 1 to 3 carbon atoms, an alkoxy group having 1 to 3 carbon atoms and an alkoxyalkyl group having 2 to 3 carbon atoms,
$R^2$ represents a straight chain, branched chain or cyclic alkyl group having 1 to 7 carbon atoms, an alkenyl having 3 to 5 carbon atoms or an alkynyl group having 3 to 5 carbon atoms,
a straight chain, branched chain or cyclic alkyl group having 1 to 7 carbon atoms substituted with a fluorine atom or atoms, a phenyl group or groups or an alkoxy group or groups having 1 to 3 carbon atoms, an alkenyl having 3 to 5 carbon atoms substituted with a fluorine atom or atoms, a phenyl group or groups or an alkoxy group or groups having 1 to 3 carbon atoms, or an alkynyl group having 3 to 5 carbon atoms substituted with a fluorine atom or atoms, a phenyl group or groups or an alkoxy group or groups having 1 to 3 carbon atoms.

3. The method according to claim 2, wherein $R^1$ is a straight chain alkyl group having 1 to 4 carbon atoms.

* * * * *